US010813774B2

(12) United States Patent
Davenport et al.

(10) Patent No.: US 10,813,774 B2
(45) Date of Patent: Oct. 27, 2020

(54) SUBJECT CONTACTING PLATE (71) Applicant: Biomet Manufacturing, LLC, Warsaw, IN (US)

(72) Inventors: Austen Davenport, Columbia City, IN (US); Kirk J. Bailey, Rochester, IN (US); Christopher Eash, Albion, IN (US); Keith R. Berend, New Albany, OH (US)

(73) Assignee: Biomet Manufacturing, LLC, Warsaw, IN (US)

( * ) Notice: Subject to any disclaimer, the term of this patent is extended or adjusted under 35 U.S.C. 154(b) by 649 days.

(21) Appl. No.: 14/639,548

(22) Filed: Mar. 5, 2015

(65) Prior Publication Data
US 2015/0250614 A1    Sep. 10, 2015

Related U.S. Application Data (60) Provisional application No. 61/949,576, filed on Mar. 7, 2014, provisional application No. 62/128,217, filed on Mar. 4, 2015.

(51) Int. Cl.
*A61F 2/46* (2006.01)
*A61B 17/92* (2006.01)
(Continued)

(52) U.S. Cl.
CPC ........ *A61F 2/4609* (2013.01); *A61F 2/30942* (2013.01); *A61F 2002/30566* (2013.01); *A61F 2002/4627* (2013.01); *A61F 2002/4629* (2013.01); *A61F 2002/4681* (2013.01); *A61F 2002/4687* (2013.01)

(58) Field of Classification Search
CPC . A61B 17/7068; A61B 17/8057; A61B 17/86; A61B 17/8605; A61B 17/8685; A61B 17/8872; A61B 17/0642; A61B 17/155; A61B 17/1742; A61F 2/30734; A61F 2002/30507; A61F 2002/30601; A61F 2002/30733; A61F 2002/30738; A61F 2002/4638; A61F 2002/4642;
(Continued)

(56) References Cited

U.S. PATENT DOCUMENTS 5,540,697 A * 7/1996 Rehmann ............... A61F 2/4609
                                                        294/95
5,571,111 A * 11/1996 Aboczky ............... A61F 2/4609
                                                        606/91
(Continued)

OTHER PUBLICATIONS

"U.S. Appl. No. 15/061,319, Restriction Requirement dated Mar. 21, 2018", 8 pgs.
(Continued)

*Primary Examiner* — Ann Schillinger
(74) *Attorney, Agent, or Firm* — Schwegman Lundberg & Woessner, P.A.

(57) ABSTRACT

An alignment plate can be designed and formed based upon a known geometry of a subject, such as a human patient. The alignment plate can include various members, such as a plurality of fingers or legs, to contact the selected points of the anatomy. Based upon contact of the fingers at the selected points of the anatomy, the alignment plate can be aligned at a preselected or predetermined alignment with a portion of the anatomy, such as an acetabulum.

19 Claims, 4 Drawing Sheets

(51) Int. Cl.
*A61B 17/88* (2006.01)
*A61F 2/30* (2006.01)

(58) Field of Classification Search
CPC ...... A61F 2002/4658; A61F 2002/4661; A61F 2002/4666; A61F 2220/0008
See application file for complete search history.

(56) References Cited

U.S. PATENT DOCUMENTS

| | | | |
|---|---|---|---|
| 5,879,402 A | | 3/1999 | Lawes et al. |
| 6,027,505 A | * | 2/2000 | Peter .................... A61F 2/4637 606/91 |
| 6,395,005 B1 | | 5/2002 | Lovell |
| 7,179,259 B1 | * | 2/2007 | Gibbs ................ A61B 17/1753 606/64 |
| 2012/0053592 A1 | | 3/2012 | Burgi |
| 2014/0276872 A1 | | 9/2014 | Song |
| 2016/0184109 A1 | | 6/2016 | Davenport et al. |

OTHER PUBLICATIONS

"U.S. Appl. No. 15/061,319, Non Final Office Action dated Jun. 15, 2018", 11 pgs.
"U.S. Appl. No. 15/061,319, Notice of Non-Responsive Amendment dated Dec. 7, 2018", 2 pgs.
"U.S. Appl. No. 15/061,319, Response filed Feb. 7, 2019 to Notice of Non-Compliant Amendment dated Dec. 7, 2018", 8 pgs.
"U.S. Appl. No. 15/061,319, Response filed Aug. 22, 2018 to Non Final Office Action dated Jun. 15, 2018", 11 pgs.
"U.S. Appl. No. 15/061,319, Response filed Nov. 13, 2019 to Final Office Action dated May 13, 2019", 10 pages.
"U.S. Appl. No. 15/061,319, Non Final Office Action dated Feb. 20, 2020", 12 pages.
"U.S. Appl. No. 15/061,319, Final Office Action dated May 13, 2019", 13 pgs.

* cited by examiner

FIG. 6

SUBJECT CONTACTING PLATE

CROSS-REFERENCE TO RELATED APPLICATIONS

This application claims the benefit of U.S. Provisional Application No. 61/949,576 filed on Mar. 7, 2014. This application claims the benefit of U.S. Provisional Application No. 62/128,217, filed on Mar. 4, 2015. The entire disclosure(s) of (each of) the above application(s) is (are) incorporated herein by reference.

FIELD

The subject disclosure relates to a system for positioning a member, and particularly to a system and method for positioning a prosthesis.

BACKGROUND

This section provides background information related to the present disclosure which is not necessarily prior art.

A prosthesis can be positioned in an anatomy, such as a human patient, for various purposes. For example, a prosthesis can be positioned to replace an articulating portion of an anatomy. In one particular example, an acetabular cup can be positioned in an acetabulum of a patient to replace damaged or diseased bone. The acetabular cup positioned within the patient can be positioned using various assemblies, such as a rod connected to the acetabular cup. However, placement of the acetabular cup is preferred to be positioned to correct for or to replicate anatomical geometries. Generally, a visual identification is used to confirm placement of the acetabular cup to achieve the anatomical geometries.

SUMMARY

This section provides a general summary of the disclosure, and is not a comprehensive disclosure of its full scope or all of its features.

A system can be used to position a member relative to a substrate or positioning a member based upon predetermined and preselected orientations. For example, an acetabular cup can be positioned within an acetabulum at a preselected and predetermined orientation, such as to achieve a selected biomechanical geometry and range of motion. It is understood, however, that a member can be positioned relative to any substrate or receiving structure, such as an aircraft, a mounting plate, a casing, or any other appropriate receiving member. Generally, an alignment member can be designed and formed to include a selected geometry that will mate complementarily with a geometry of a substrate to guide an implanting or positioning member through a rod and an alignment plate.

According to various embodiments, an alignment plate can be designed and formed based upon a known geometry of a subject, such as a human patient. The alignment plate can include various members, such as a plurality of fingers or legs, to contact the selected points of the anatomy. Based upon contact of the fingers at the selected points of the anatomy, the alignment plate can be aligned at a preselected or predetermined alignment with a portion of the anatomy, such as an acetabulum. Once the plate is aligned, an acetabular cup can be impacted into the acetabulum at the preselected and predetermined geometry to achieve a predetermined and preselected alignment and placement of the acetabular cup.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 B is a bottom view of an alignment plate;

Corresponding reference numerals indicate corresponding parts throughout the several views of the drawings.

DETAILED DESCRIPTION

Example embodiments will now be described more fully with reference to the accompanying drawings.

Figures 1, 2A:
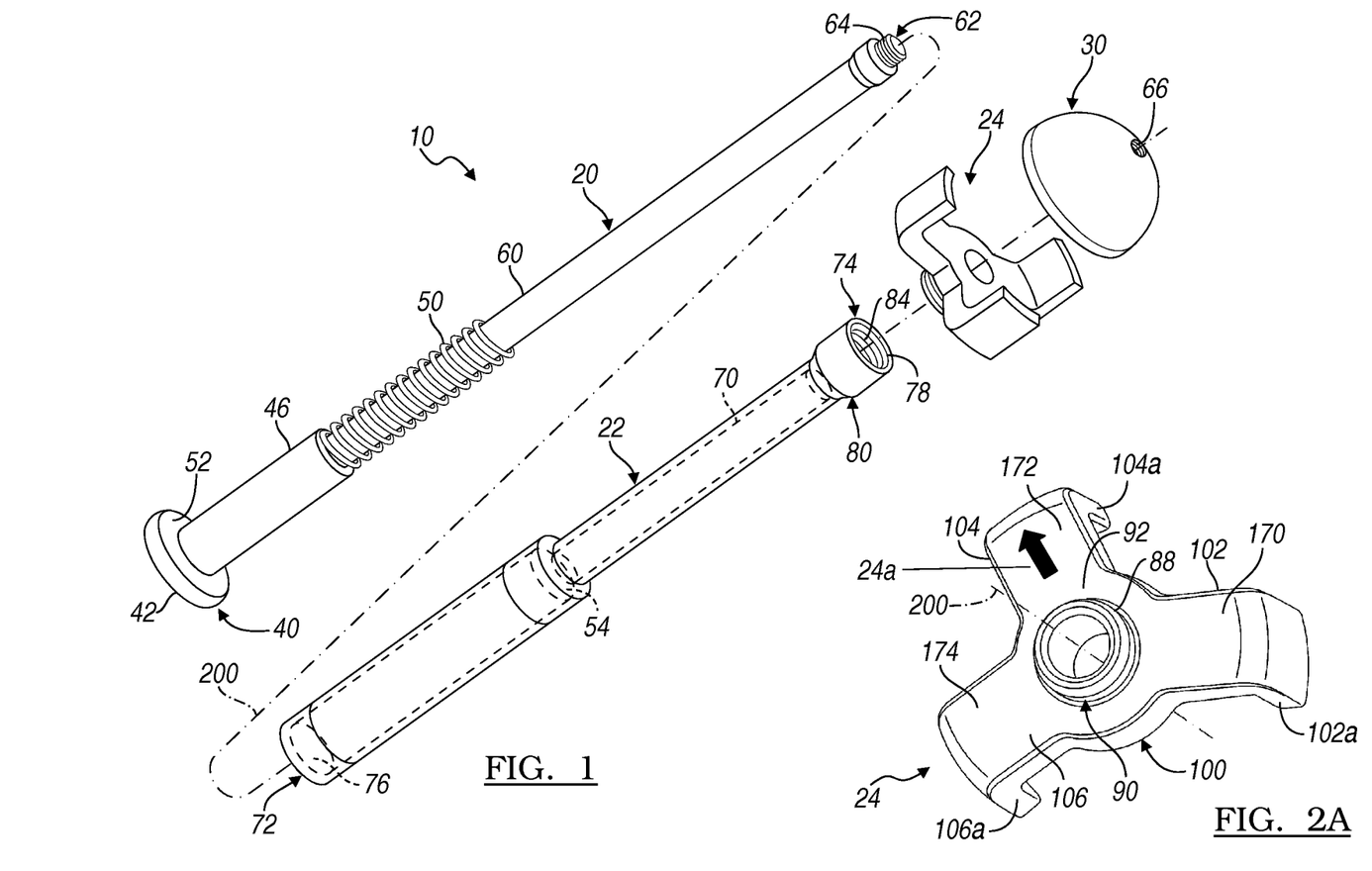
FIG. 1 is an exploded view of an alignment and implantation system, according to various embodiments.
FIG. 2A is a top view of an alignment plate.

According to various embodiments an implantation assembly 10 can include an impaction rod 20, an impaction sleeve 22, and an alignment plate 24. The assembly of the impaction rod 20, the impaction sleeve 22, and the alignment plate 24 may be used to position and implant a prosthesis, such as an acetabular prosthesis 30, into an acetabulum, as discussed further herein. Generally, the acetabular cup 30 can be interconnected with the impaction rod 20, as discussed further herein, to be positioned into a selected anatomy. After positioning of the acetabular cup 30 into the anatomy, the impaction rod 20 can be disconnected from the acetabular cup 30 and the implantation assembly 10 can be removed from the acetabular cup 30 and the selected patient to allow for completion of a procedure.

Figures 4, 5:
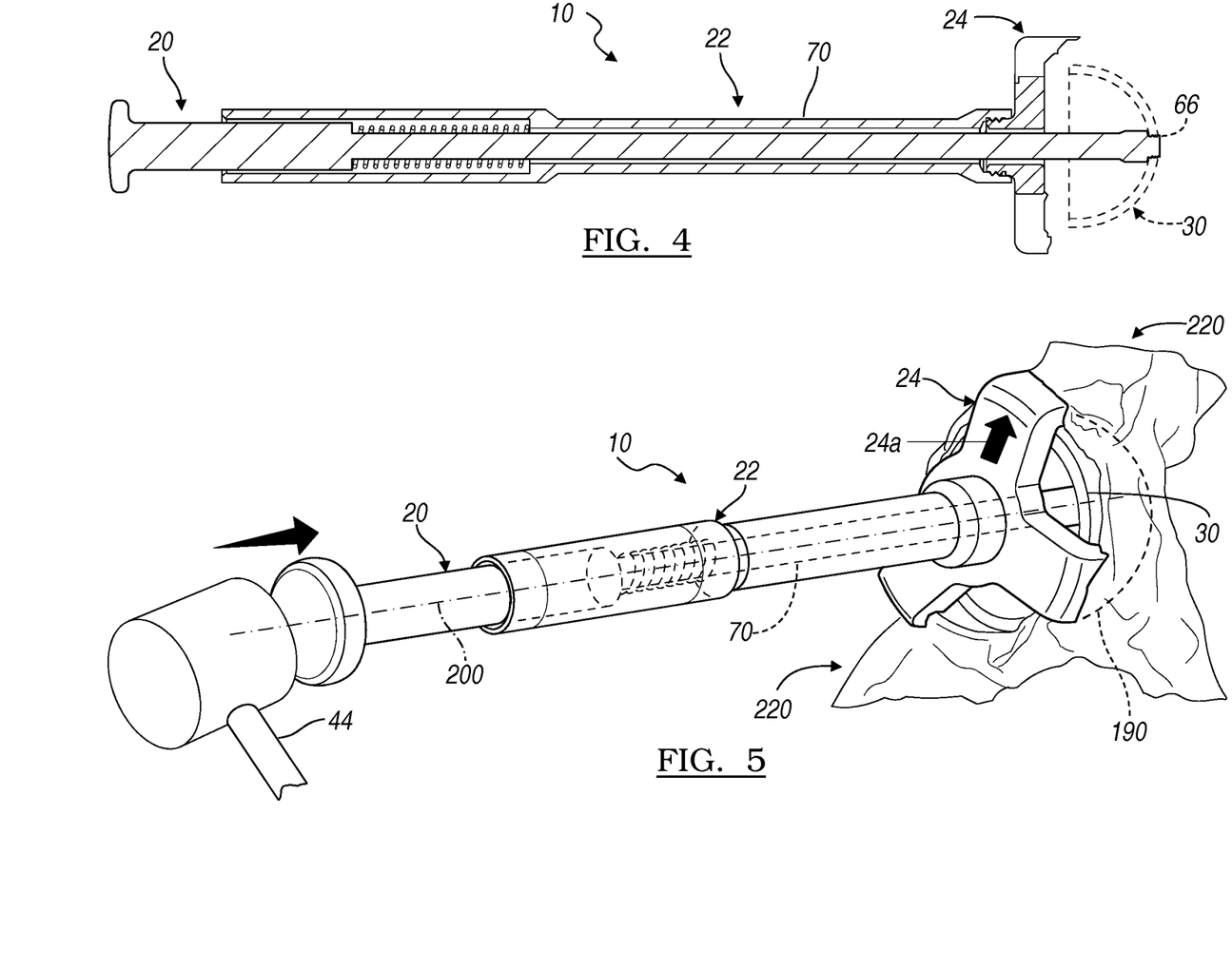
FIG. 4 is an assembled cross-sectional view of the implantation and alignment assembly.
FIG. 5 is an environmental view of the implantation and alignment assembly.

According to various embodiments, the impaction rod 20 can include an impaction head or portion 40 that has an impaction surface 42 that can be struck or impacted with a selected implement, such as a mallet 44 (FIG. 4). The impaction rod 20 can have the impaction head 40 interconnected with a first section 46 that can have a selected diameter that is equal to, less than, or greater than a diameter of the impaction head 40. Generally, the impaction head 40 can extend beyond the first rod section 46 to allow for a large surface area for receiving the impaction mallet 44.

Further, according to various embodiments, a spring 50 can be positioned near the first section 46 and to contact a second surface or spring surface 52 of the first section or the impaction head 40. The spring 50 can engage a ledge or wall 54 within the impaction sleeve 22. The spring 50, when engaging the ledge 54, can hold the impaction rod 20 in a selected position relative to the impaction sleeve 22. Further, the spring 50 can act as a rebound spring to position the impaction rod 20 at a distance away from the impaction sleeve 22 or the alignment plate 24 in at least an initial position of the impaction rod 20 relative to the alignment plate 24 and a selected anatomy.

The impaction rod 20 may further include a second section 60 that extends from the first section 46. The second section 60 can include a diameter that is the same as or different than the first section 46, such as larger or smaller in diameter to the first section 46. The second section 60 extends from the first section 46 and may terminate in a prosthesis or acetabular cup engaging the portion 62. The acetabular cup engaging portion 62 can include an externally threaded portion that includes external threads 64 that may engage internal threads 66 in the acetabular cup 30. The internal thread 66 can be generally known threads in an apical hole, such as threads included in the G7™ acetabular cup system and/or the Ringloc® acetabular cup system, sold by Biomet, Inc., having a place of business in Warsaw, Ind. The implant or cup engaging region 62, therefore, can be generally similar to or identical to generally known cup engaging regions.

The alignment sleeve 22 can be formed to align or position the impaction rod 20 relative to the acetabular cup 30. For example, the alignment sleeve 22 can include an internal bore 70 through which the impaction rod 20 is configured to pass. The internal diameter of the internal bore 70, therefore, can include an internal diameter that can slidably engage the impaction rod 20. The internal diameter of the internal bore 70 can allow for space between the impaction rod 20 and a wall that defines the internal bore 70 and need not include a tight or contacting fit. In other words, the rod 20 can freely pass through the sleeve 22 for engaging the acetabular cup 30, as discussed herein. Generally, the impaction sleeve 22 can include a first or proximal end 72 through which the impaction rod 20 can initially pass to a second or distal end 74. The proximal end 72 can include an opening 76 to the internal bore 70 through which the impaction rod 20 can pass. The second end 74 can include a second opening 78 through which at least the cup connection region 62 can pass to engage the acetabular cup 30 through the alignment plate 24.

Formed near or at the second end 74 can be an alignment plate engaging region or section 80. The alignment plate engaging region 80 can include internal thread or any other appropriate connection portion 84 to engage the alignment plate 24. In various embodiments, the alignment plate engaging portion can include a taper connection, a snap ring, a bayonet slot connection, etc. As illustrated, the internal thread 84 can engage an external thread 88 on a sleeve engaging region 90 of the alignment plate 24, as further illustrated in FIG. 2A. The external thread 88 can threadably engage, such as by rotation, the internal thread 84 of the alignment sleeve 22 to hold the alignment plate 24 relative to and fixed to the alignment rod 20 for a selected procedure. A terminal or external surface of the second end 74 can engage the alignment plate 24, such as a top or exterior facing surface 92 of the alignment plate 24, to ensure an appropriate, known, and preselected position alignment of the alignment plate 24 relative to the alignment rod 20. For example, the connection of the alignment plate 24 to the sleeve 22 can ensure that at least the top surface 92 of the alignment plate 24 is orthogonal to a long axis of the sleeve 22.

Figure 2B:
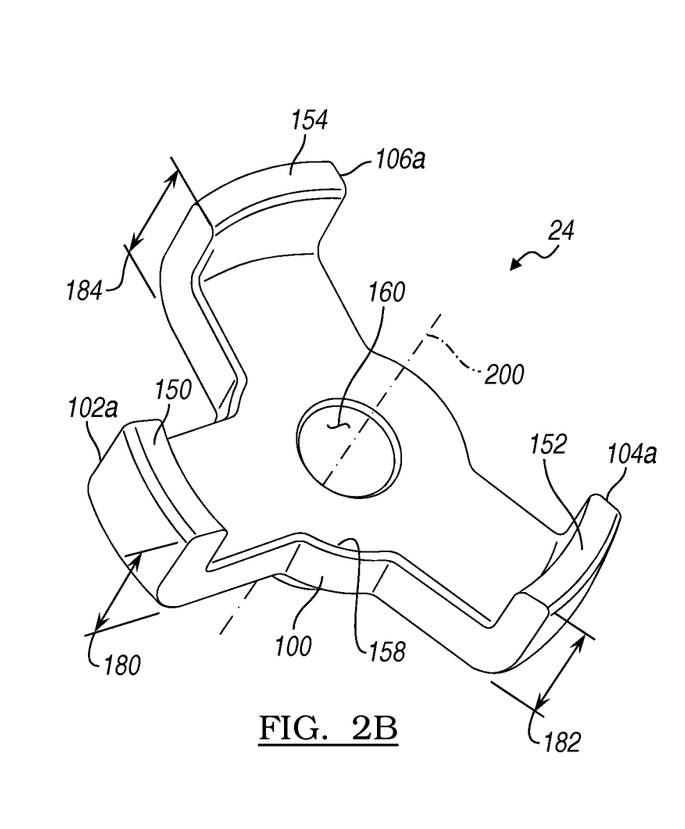

With continuing reference to FIG. 1 and additional reference to FIGS. 2A and 2B, the alignment plate 24 can be held to the alignment sleeve 22 for a selected procedure, such as implanting or positioning the acetabular cup 30. According to various embodiments, the alignment plate 24 can include a central hub region 100 from which the sleeve engaging section 90 can extend to engage the alignment sleeve 22. It is understood, however, that the alignment plate 24 can include a female or negative receiving or engaging region to engage in alignment sleeve 22. Accordingly, a positive or extending region 90 is not required to extend from the hub portion 100.

Further, according to various embodiments, one or a plurality of engaging legs or fingers 102, 104 and 106, can extend from the central hub region 100. Although illustrated are three fingers 102-106 included with the alignment plate 24, having three fingers is not a requirement. For example, less than or more than three fingers may be selected or included. As discussed herein, the number of fingers can be selected during a design and manufacture process based on design criteria, such as patient matching.

Extending away from the central hub 100, and generally directed away from the sleeve engaging portion 90, may be tabs 102a, 104a, and 106a that extend at an angle from the respective fingers 102-106 and generally away from the alignment sleeve 22. As discussed further herein, the respective tabs 102a-106a can engage selected portions of the anatomy to ensure appropriate alignment of the alignment plate 24 relative to the selection portion of the anatomy. Through connection of the alignment sleeve 22 with the alignment plate 24 appropriate alignment of the alignment sleeve 22 and the impaction rod 20 are achieved. Accordingly, the plurality of fingers 102-106 and the plurality of tabs 102a-106a can be used to ensure appropriate alignment of the alignment sleeve 22 and the alignment impaction rod 20 with the selected anatomy to ensure positioning of the acetabular cup 30 in the anatomy in an appropriate and preselected alignment and position.

With continued reference to FIGS. 1 and 2A, and additional reference to FIG. 2B, the alignment plate 24 can include the three tabs 102a, 104a, and 106a. Each of the tabs 102a-106a can terminate in respective bone contacting surfaces 150, 152, and 154. Each of the bone contacting surfaces 150-154 can extend away from a bottom surface or implanting facing surface 158 of the central hub 100. A throughbore 160 may be formed through the sleeve engaging portion 90 and the bottom surface 158 to allow the impaction rod 20 to engage the acetabular cup 30, as discussed further herein.

Each of the bone contacting surfaces 150-154 that are at a bottom or terminus of the respective tabs 102a-106a can extend a selected distance from a respective top surface 170, 172, 174 of each of the respective fingers 102-106 (as illustrated in FIG. 2A). For example, the first bone contacting surface 150 can extend a distance 180 from the upper surface 170 of the alignment plate 24. The second bone contacting surface 152 can extend a distance 182 from the upper surface 172 of the alignment plate 24. The third bone contacting surface 154 can extend a distance 184 from the upper surface 174 of the alignment plate 24. Each of the respective distances 180-184 can be determined and preselected based upon boney portions of an anatomy, such as boney portions adjacent or near an acetabulum 190 (as illustrated in FIG. 4). The boney portions can be selected to be spaced about the acetabulum 190 such as at a position stabilize the alignment plate 24 during implantation and impaction of the acetabular cup 30. For example, the boney prominences or high points may be positioned or at or near the ilium, the pubis, and the ischium. As illustrated in FIG. 2A and FIG. 5 an indicator 24*a* can be provided to assist in at least initial alignment and/or placement of the plate 24 relative to the anatomy. For example, the indicator 24*a* can include an arrow that is to be pointed towards the iliac crest when properly aligned. The boney portions that are contacted by the bone contacting surfaces 150-154, however, can be at any appropriate portion near the acetabulum 190 and above are merely examples.

The selected distances 180-184 can be selected based upon an appropriate or selected orientation, including a version angle of the cup 30, relative to the acetabulum 190 of the sleeve 22 and the impaction rod 20 during impaction of the acetabular cup 30 into the acetabulum 190. As is understood, the three distances 180-184 will orient an axis 200 that extends through the assembly 10 (including the assembled impaction rod 20, sleeve 22, and alignment plate 24) and the acetabular cup 30 when the bone contacting surfaces 150-154 contact the bone portion adjacent to the acetabulum 190. Accordingly, an orientation of the axis 200 relative to the acetabulum 190 can be selected and achieved based upon the respective distances 180-184 to achieve a preselected orientation of the acetabular cup 30 relative to the acetabulum 190. Further, the orientation and angle of the axis 200 can be preselected based upon an analysis and selected orientation of the acetabular cup 30 in the acetabulum 190.

Achieving the selected orientation of the axis 200 relative to the acetabulum 190 may be preselected based on various selections, such as anatomical geometry and desired range of motion after implantation. The orientation may be achieved with appropriate mechanisms, such as review and analysis of image data of the acetabulum 190 prior to a procedure. For example, various procedures and systems can obtain image data of portions of an anatomy, such as a computer tomography (CT) Scan, a magnetic resonance image (MRI) scan, a plurality of two-dimensional images, and the like of a patient for determining a post-implantation orientation of an acetabular cup 30 relative to the acetabulum 190.

According to various embodiments, a user, such as a surgeon may determine the selected angle of the sleeve 22 and/or rod 20. A manufacturer of the plate 24 may then determine the lengths 180-184 to achieve the selected angle. It is further understood, that the user may provide to the manufacturer only a selected final implantation orientation of the cup 30 and the manufacturer then analyzes the image data to determine the required angle of the sleeve 22 and/or rod 20 and then the required lengths 180-184. Thus, a user need to not determine manufacturing specifications, but may only be required to provide to a manufacturer a desired or selected final implantation orientation of the selected prosthesis.

Figure 3A:
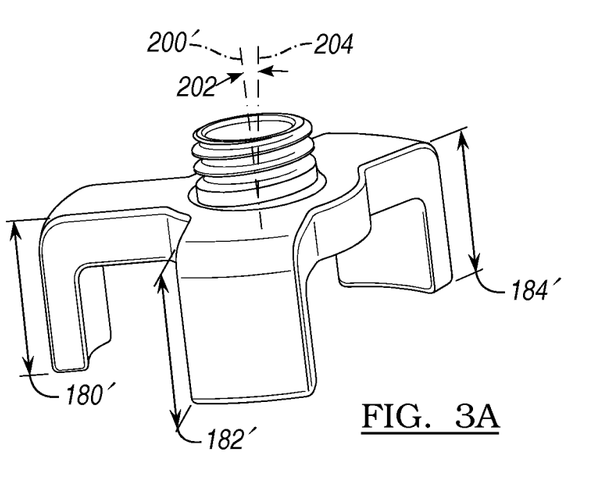
FIG. 3A is a plan view of a first configuration of the alignment plate to achieve a first orientation, according to various embodiments.
Figure 3B:
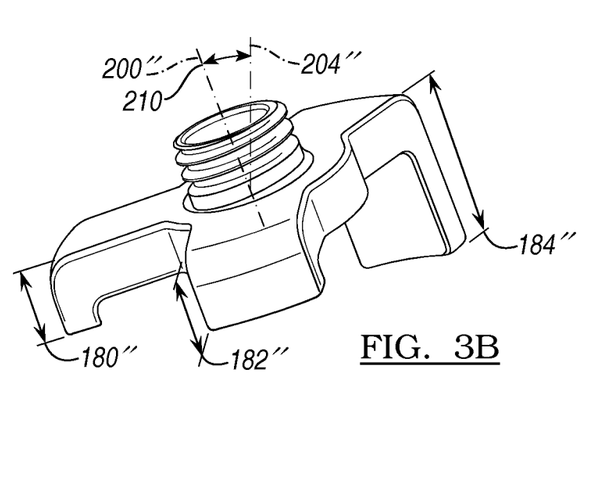
FIG. 3B is a plan view of a second configuration of the alignment plate to achieve a second orientation, according to various embodiments.

As an example, and not limit the appropriate or selectable lengths 180-184, FIGS. 3A and 3B illustrate two variations of the axis 200 relative to a perpendicular line 204. For example, as illustrated in FIG. 3A, the distances 180'-184' may be formed in the plate 24 such that the axis 200' is at a first angle 202 relative to the perpendicular line or axis 204. The angle 202 can be an appropriate angle, such as about 2°. With reference to FIG. 3B, the distances 180-184 are illustrated as 180"-184". The distance 184" can be greater than the distance 184' such that the axis 200" is at an angle 210 relative to the perpendicular line 204. The angle 210 may be greater than the angle 202, such as about 7°-10°. Accordingly, based upon analysis and selection by a user, such as a surgeon, the appropriate or implanted angle of the acetabular cup 30 can be selected and then achieved by selecting lengths 180-184 of the alignment plate 24 to achieve the selected angle.

According to various embodiments, the alignment plate 24 can be designed, manufactured, and produced based upon a selected individual patient. Accordingly, each patient can have the patient's own specific or patient-specific alignment plate 24 to achieve an appropriate alignment of the axis 200 relative to the acetabulum 190 of the specific patient. Appropriate alignment of the axis 200 can be achieved based upon analysis of the image data. According to various embodiments, the analysis can be achieved by analysis of image data, such as similar to the Signature™ patient matched system offered by Biomet, Inc. and/or the systems and methods as discussed in U.S. Patent App. Pub. No. 2011/0166578; 2011/01980899; or 2011/0015639; or U.S. Pat. No. 8,407,067 or 8,070,752, incorporated herein by reference.

The plate 24, therefore, including the lengths 180-184 may be designed after analysis of a patient, such as analysis of image data. The analysis and the desired angle can be determined and the plate 24 may be designed to achieve the alignment of the system 10 for implantation of the cup 30. Thus, the plate 24 may be manufactured after the analysis and determination of the desired and selected angle. Accordingly, each plate 24 may be designed and manufactured for substantially a single use with a specific procedure, such as a single patient.

The manufacture of the plate 24 may be performed in any appropriate manner. For example, a rapid prototyping or three-dimensional printing may be used to form the plate 24. Also, the plate 24 may be made of a polymer material that may efficiently and quickly molded into a selected shape, such as with injection molding. Moreover, the plate 24 may be machined, such as a with controlled machining, to achieve the selected dimensions to achieve the selected alignment.

With additional reference to FIGS. 4 and 5, the implantation assembly 10 can be assembled such that the impaction rod 20 is passed through the sleeve 22, such as passing the impaction rod 20 through the internal bore 70 of the sleeve 22 and through the alignment plate 24 to engage the apical thread 66 of the acetabular cup 30, as illustrated in FIG. 4. The alignment plate 24 may be threaded onto the sleeve 22 prior to passing the impaction rod 20 through the sleeve 22 to engage the acetabular cup 30. Accordingly, as illustrated in FIG. 4, the assembly can include the sleeve 22 attached to the alignment plate 24 and the impaction rod 20 attached to the acetabular cup 30. The rod 20 may be attached to the acetabular cup 30 after the assembly of the sleeve 22 to the alignment plate 24 and passing the rod 20 through the sleeve 22 and plate 24. Once assembled, as illustrated in FIG. 5, the alignment plate 24 can engage the selected boney portions of a pelvis 220 near or adjacent to the acetabulum 190. By the alignment plate 24 engaging the boney portions adjacent to the acetabulum 190, it may align the axis 200 as preselected or predetermined. As noted above, the indicator 24*a* may be provided and/or used to assist in at least initial alignment of the plate 24 with the pelvis 220 and the selected boney portions. For example, the indicator 24*a* may be the arrow that is to be pointed towards the iliac crest when the plate 24 is aligned properly. The bone engaging surfaces contacting the boney portions will align the axis 200 relative to the acetabulum 190 as preselected prior to the procedure and the acetabular cup 30 is appropriately aligned within the acetabulum 190 prior to impaction of the acetabular cup 30 into the acetabulum 190.

Once appropriately aligned, the mallet 44 may be used to engage in a selected manner, such as a forceful manner, the impaction rod 20. By impacting the impaction rod 20, the acetabular cup 30 will be engaged into the acetabulum 190. It is understood that various acetabular cups can be impacted into the acetabulum 190, such as substantially cementless acetabular cups. It is further understood, however, that various cements can be positioned in the acetabulum 190 prior to impaction. It is understood, therefore, that the cup 30 may be held in the acetabulum by a cement material and impaction with the mallet 44 may not be required. In a cemented system, the cup 30 may be placed in a cement mantle and the system 10 may be used essentially to ensure only appropriate and selected alignment rather than also providing the rod 20 for a forceful impaction of the cup 30.

Accordingly, once the acetabular cup 30 is implanted, such as by placement and/or impaction in the acetabulum, the impaction rod 20 can be disengaged from the acetabular cup 30 such as by unthreading the impaction rod 20 from the acetabular cup 30. Once the impaction rod 20 is unthreaded from the acetabular cup 30, the sleeve 22 and the alignment plate 24 are free to be removed from contact with the pelvis 220. Accordingly, the acetabular cup 30 may be implanted in a preselected alignment and orientation within the acetabulum 190 based upon the distances 180-184 as discussed above.

Figure 6:
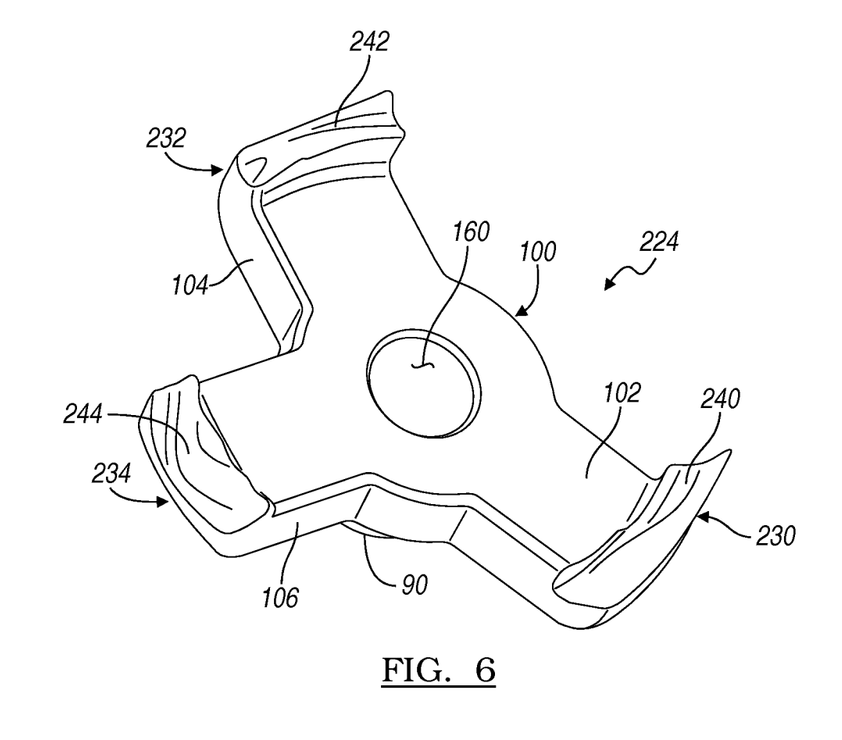
FIG. 6 is an alignment plate, according to various embodiments.

According to various embodiments, with reference to FIG. 6, an alignment plate 224 is illustrated. The alignment plate 224 can be substantially similar to the alignment plate 24 discussed above, and include the central hub 100, the sleeve engaging portion 90, the one or more fingers 102-106, and the throughbore 160. The alignment plate 224 can differ from the alignment plate 24 in the configuration and design of bone engaging surfaces.

As discussed above, tabs may extend from each of the fingers 102-106. For example, a first tab 230 can extend from the finger 102, a second tab 232 can extend from the second finger 104, and a third tab 234 can extend from the third finger 106. Each of the tabs 230-234 include substantially patient-specific bone engaging surfaces 240, 242, and 244, respectively. Each of the patient-specific bone engaging surfaces 240-244 can engage such portions of the anatomy, such as boney protrusions or high points on the pelvis 220 near the acetabulum 190 similar to the bone engaging surfaces 150-154.

The patient-specific bone engaging surfaces 240-244, however, include contours, shapes, and the like that are substantially complementary or mirror images of the bone portions of the pelvis 220. Forming such patient-specific geometries of the bone engaging surfaces 240-244 includes obtaining image data of the patient and subtracting from the tabs 230-234 the geometry of the bone. Thus, the patient-specific bone engaging surface 240-244 will engage substantially only a single and unique portion of the anatomy of a single patient. This can assist in reducing time in performing a procedure as the plate 24 will only fully engage and seat against the pelvis 220 in a single orientation.

The geometry of the alignment plate 224, however, can be altered including selecting or adjusting heights or distances of the bone engaging surfaces 240-244 from respective top surfaces of the alignment plate 224 to achieve alignment as discussed above. The specific engagement of the patient-specific bone engaging surfaces 240-244, however, can also help ensure that the alignment plate 224 is positioned at the specified and predetermined orientation relative to the anatomy.

It is understood that the bone engagement surfaces 240-244 can engage other hard portions of the anatomy that are not bone, such as cartilage, calcified regions, spurs, and the like. Further, the bone engagement surfaces 150-154 can similarly engage non-bone portions of the anatomy as selected to achieve an appropriate alignment. Thus, the bone contacting surfaces, according to the various embodiments, can engage any appropriate portion of the anatomy near the acetabulum to achieve the selected alignment of the system 10.

Accordingly, as discussed above, the positioning assembly 10 can be used to position an implant, such as the acetabular prosthesis 30 relative to the anatomy, including the acetabulum 190. It is understood that the assembly 10, however, can be used to position any appropriate prosthesis, such as a femoral head prosthesis, femoral stem prosthesis, humeral head prosthesis, glenoid prosthesis, or other appropriate prostheses. The alignment plate 24, 224 can be designed and manufactured with bone engaging or hard surface engaging portions to achieve an alignment of the sleeve 22 and the impaction rod 20 to implant the prosthesis in any appropriate manner. Accordingly, it is understood, that although discussed above is an exemplary instrument assembly to implant an acetabular prosthesis that appropriate prostheses can be implanted with the assembly 10 in an appropriate manner as understood by one skilled in the art.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for placing an acetabular cup, comprising:
    a first member extending from a first end to a second end, the second end configured to fixedly engage an acetabular cup;
    a sleeve member having a length shorter than the first member and comprising a throughbore extending through the sleeve member configured to slidably receive the first member, and an alignment plate engaging portion at a distal end of the sleeve member to hold an alignment plate relative to the sleeve member during movement of the first member; and
    the alignment plate including a throughbore through which the first member is configured to extend and at least one finger extending from a central region to at least one engaging surface, the at least one finger configured to extend outside of an outer circumference of the acetabular cup during placement, the at least one engaging surface configured to engage a portion of a subject to align the alignment plate and the first member relative to the subject in a predetermined orientation;
    wherein the first member is configured to move relative to the alignment plate;
    wherein the system is configured for placement of the acetabular cup.

2. The system of claim 1, wherein the at least one engaging surface is spaced a distance from a central surface of the central region.

3. The system of claim 1, wherein the at least one finger includes at least three fingers extending radially from the central region and spaced around the central region.

4. The system of claim 3, wherein each of the at least three fingers has at least one of the at least one engaging surface;
wherein each of the at least one engaging surface is configured to selectively engage a portion of the subject during positioning of a prosthesis with the first member.

5. The system of claim 4, wherein each finger of the at least three fingers includes a tab, wherein each at least one engaging surface is formed on the tab;
wherein at least one tab of at least one finger has a length different than at least one other tab of at least the other two fingers.

6. The system of claim 2, further comprising:
a spring positioned between the first member and the sleeve to resiliently position the first member relative to the sleeve member.

7. The system of claim 1, wherein the first member is configured to fixedly engage the acetabular cup via a threaded connection.

8. A system for placing an acetabular cup, comprising:
a rod extending from a first rod end to a second rod end, the second rod end configured to fixedly engage an acetabular cup;
a sleeve having a length shorter than the rod, the sleeve extending from a first sleeve end to a second sleeve end having a through bore extending through the sleeve configured to slidably receive the rod member and an alignment plate engaging portion at a distal end of the sleeve to hold an alignment plate relative to the sleeve during movement of the first member; and
the alignment plate comprising:
a through bore through which the rod is configured to extend,
a first finger and a second finger both extending from a central region through which the through bore extends, wherein the first finger is spaced a distance from the second finger around the central region, wherein each of the first and second fingers is configured to extend outside an outer circumference of the acetabular cup during placement, and
a first subject engaging surface extending a first distance from the first finger and a second subject engaging surface extending a second distance from the second finger,
wherein first distance and the second distance are selected to achieve a preselected alignment of at least one of the rod or the sleeve when the sleeve is engaged to the alignment plate and the first subject engaging surface and the second subject engaging surface are engaging the subject;
wherein the rod is configured to slide relative to the alignment plate;
wherein the system is configured for placement of the acetabular cup.

9. The system of claim 8, wherein the alignment plate further includes
a third finger extending from the central region, wherein the third finger is spaced a distance from both the first finger and the second finger around the central region, and
a third subject engaging surface extending a third distance from the third finger.

10. The system of claim 9, wherein all of the first subject engaging surface, the second third subject engaging surface, and the third subject engaging surface are sized to engage an anatomical projection near an acetabulum of a human subject.

11. The system of claim 9, wherein the first subject engaging surface is configured to engage a projection near an ilium, the second third subject engaging surface is configured to engage a projection near a pubis, and the third subject engaging surface is configured to engage a projection near an ischium.

12. The system of claim 8, wherein the alignment plate includes an external thread and the alignment plate engaging portion includes an internal thread to threadably engage the external thread.

13. The system of claim 12, wherein the sleeve is configured to be assembled to the alignment plate prior to sliding the rod through the through bore of the sleeve.

14. A method of selecting an alignment of a system, comprising:
selecting a dimension of at least a first tab of at least one finger of an alignment plate based at least on an analysis of a subject to achieve a selected alignment of a sleeve relative to the subject;
designing the alignment plate to include the at least the first tab having the selected dimension;
forming the alignment plate to include the at least the first tab having the selected dimension; and
providing the formed alignment plate for use in a procedure to place an acetabular cup, wherein the alignment plate includes:
a first member extending from a first end to a second end, the first member configured to fixedly engage the acetabular cup,
the sleeve having a length shorter than the first member and comprising a throughbore extending through the sleeve configured to slidably receive the first member, and an alignment plate engaging portion at a distal end of the sleeve to hold the alignment plate relative to the sleeve during movement of the first member, and
the alignment plate including a through bore through which the first member is configured to extend and the at least one finger extending from a central region to at least one engaging surface, the at least one finger configured to extend outside of an outer circumference of the acetabular cup during placement, the at least one engaging surface configured to engage a portion of a subject to align the alignment plate and the first member relative to the subject in a predetermined orientation, wherein the first member is configured to move relative to the alignment plate.

15. The method of claim 14, further comprising:
evaluating image data of the subject and to select the dimension to achieve the selected alignment of the sleeve.

16. The method of claim 15, further comprising:
receiving the selected alignment of the sleeve from a user.

17. The method of claim 15, further comprising:
receiving a selected alignment of the acetabular cup after implantation into the subject; and
determining the selected alignment of the sleeve to achieve the selected alignment of the acetabular cup in the subject.

18. The method of claim 14, wherein forming the alignment plate includes manufacturing the alignment plate with an additive manufacturing process.

19. The method of claim 14, further comprising:
designing the alignment plate to include at least a second tab having a selected second dimension; and forming the alignment plate to include the at least the second tab having the selected second dimension;

wherein the first dimension is different from the second dimension.

\* \* \* \* \*

UNITED STATES PATENT AND TRADEMARK OFFICE
CERTIFICATE OF CORRECTION

PATENT NO.        : 10,813,774 B2
APPLICATION NO.   : 14/639548
DATED             : October 27, 2020
INVENTOR(S)       : Davenport et al.

Page 1 of 1

It is certified that error appears in the above-identified patent and that said Letters Patent is hereby corrected as shown below:

In Column 9, Line 16, in Claim 6, delete "claim 2," and insert --claim 1,-- therefor Signed and Sealed this
Twelfth Day of January, 2021

Andrei Iancu
*Director of the United States Patent and Trademark Office*